US006106859A

United States Patent [19]

Densmore, Jr. et al.

[11] Patent Number: 6,106,859

[45] Date of Patent: Aug. 22, 2000

[54] STABILIZATION OF LIPID:DNA FORMULATIONS DURING NEBULIZATION

[76] Inventors: Charles L. Densmore, Jr., 83 S. Copper Sage Cr., The Woodlands, Tex. 77381; J. Vernon Knight, 29 Lana La., Houston, Tex. 77027; J. Clifford Waldrep, 6 Wind Trace Ct., The Woodlands, Tex. 77381; Berma M. Kinsey, 3702 Elmore St., Houston, Tex. 77005

[21] Appl. No.: 09/227,648

[22] Filed: Jan. 8, 1999

Related U.S. Application Data

[60] Provisional application No. 60/071,052, Jan. 8, 1998.

[51] Int. Cl.$^7$ .......................... A61K 9/127; A61K 51/00; C12N 15/88

[52] U.S. Cl. ......................... 424/450; 424/450; 424/1.21; 435/458

[58] Field of Search .................................. 424/1.21, 450; 435/458

*Primary Examiner*—Bruce R. Campell
*Assistant Examiner*—Richard Schnizer
*Attorney, Agent, or Firm*—Benjamin Aaron Adler

[57] ABSTRACT

The present invention provides a liposomal aerosol composition, comprising a pharmaceutical compound, a cationic lipid, (c) a neutral co-lipid; and (d) tryptone. Also provided is a nebulized cationic lipid:DNA suspension useful for lipid-DNA transfections, wherein said cationic lipid is bis(guanidinium)-tren-cholesterol.

3 Claims, 5 Drawing Sheets

STABILIZATION OF LIPID:DNA FORMULATIONS DURING NEBULIZATION

Provisional Application Ser. No. 60/071,052 filed Jan. 8, 1998.

BACKGROUND OF THE INVENTION

1. Field of the Invention

The present invention relates generally to the fields of lipid/liposome technology and DNA delivery. More specifically, the present invention relates to a stabilization of lipid:DNA formulations during nebulization.

2. Description of the Related Art

The development of liposomal formulations compatible with aerosol delivery has allowed the jet nebulizer to deliver nucleic acids preparations whose biological activity is maintained sufficient for therapeutic use. Utilization of liposomes for aerosol delivery has many advantages, including aqueous compatibility; sustained pulmonary release allowing maintanence therapeutic drug levels; and, further, liposomes facilitate intra-cellular delivery, particularly to respiratory epithelial cells.

The efficacy of localized, topical therapy via aerosols is determined by the amount of drug delivered at the sites of disease within the lung; and there are several different key parameters that determine the amount of delivery which interact to provide the therapeutic efficacy of aerosol formulations. For example, nebulizer design, flow rate, flow volume, particle size, hygroscopicity and the presence of ancillary equipment (tubing, connectors, mouth pieces, face masks, and the like), are important variables. Thus, aerosol output efficiency of appropriate particle sizes can be increased through proper implementation of the proper nebulizer device. Inappropriate implementation of the device and/or imperfect parameters can affect inhaled dosages, delivery sites and influence the therapeutic outcome.

Drug formulation also is a critical factor regulating aerosol output efficiency and aerodynamic properties of drug-liposomes. It has been discovered that drug-liposome output efficiency can be increased through the utilization of liposomes formulated with low phase transition temperatures (see Waldrep et al., *J. of Aerosol Med.* 7:1994 (1994) and Waldrep et al., *Int'l J. of Pharmaceutics* 97:205–12 (1993)). An additional method to increase aerosol drug-liposome output is to increase the drug and phospholipid reservoir concentrations. Nebulization of some drug-liposome formulations at greater than 50 mg/ml results in clogging of the nebulizer jets; yet empty liposomal formulations up to 150 mg/ml have been successfully nebulized (see Thomas, et al., *Chest* 99:1268–70 (1991)). Further, the aerosol performance (output and particle size) is influenced in part by physiochemical properties such as viscosity and surface tension. Such variables affect the maximal drug-liposome concentrations compatible with aerosol delivery via the jet nebulizer.

A problem associated with the aerosol delivery of cationic lipid:plasmid DNA formulations for the purpose of targeted pulmonary gene therapy is that the process of nebulization leads to a marked decrease in the transfection efficiency of the formulations. This is a major reason for the relatively low in vivo gene transfer efficiency of aerosolized formulations. A rapid loss in activity is associated with a wide variety of jet nebulizers and lipid:DNA formulations.

The prior art is deficient in the lack of effective means of improving the stabilization of lipid:DNA formulations during nebulization. The present invention fulfills this long-standing need and desire in the art.

SUMMARY OF THE INVENTION

In one embodiment of the present invention, there is provided a liposomal aerosol composition, comprising: (1) a pharmaceutical compound, (2) a cationic lipid, (3) a neutral co-lipid, and (4) tryptone.

In another embodiment of the present invention, there is provided a liposomal aerosol composition, comprising: (1) a pharmaceutical compound; (2) a cationic lipid, (3) a neutral co-lipid, and (4) glutamic acid.

In yet another embodiment of the present invention, there is provided a nebulized cationic lipid:co-lipid:DNA suspension useful for lipid-DNA transfections, wherein said cationic lipid is bis(guanidinium)-tren-cholesterol (BGTC).

In still yet another embodiment of the present invention, aerosol exposure was made more efficient and more effective by holding mice in a closed chamber and exposing to aerosol that was replenished during a one minute period of nebulization out of each minutes period. In this design, compressed air containing 5% carbon dioxide was used instead of room air in order to enhance the deep breathing of animals and thereby enhance the lung deposition of the transfection formulations.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
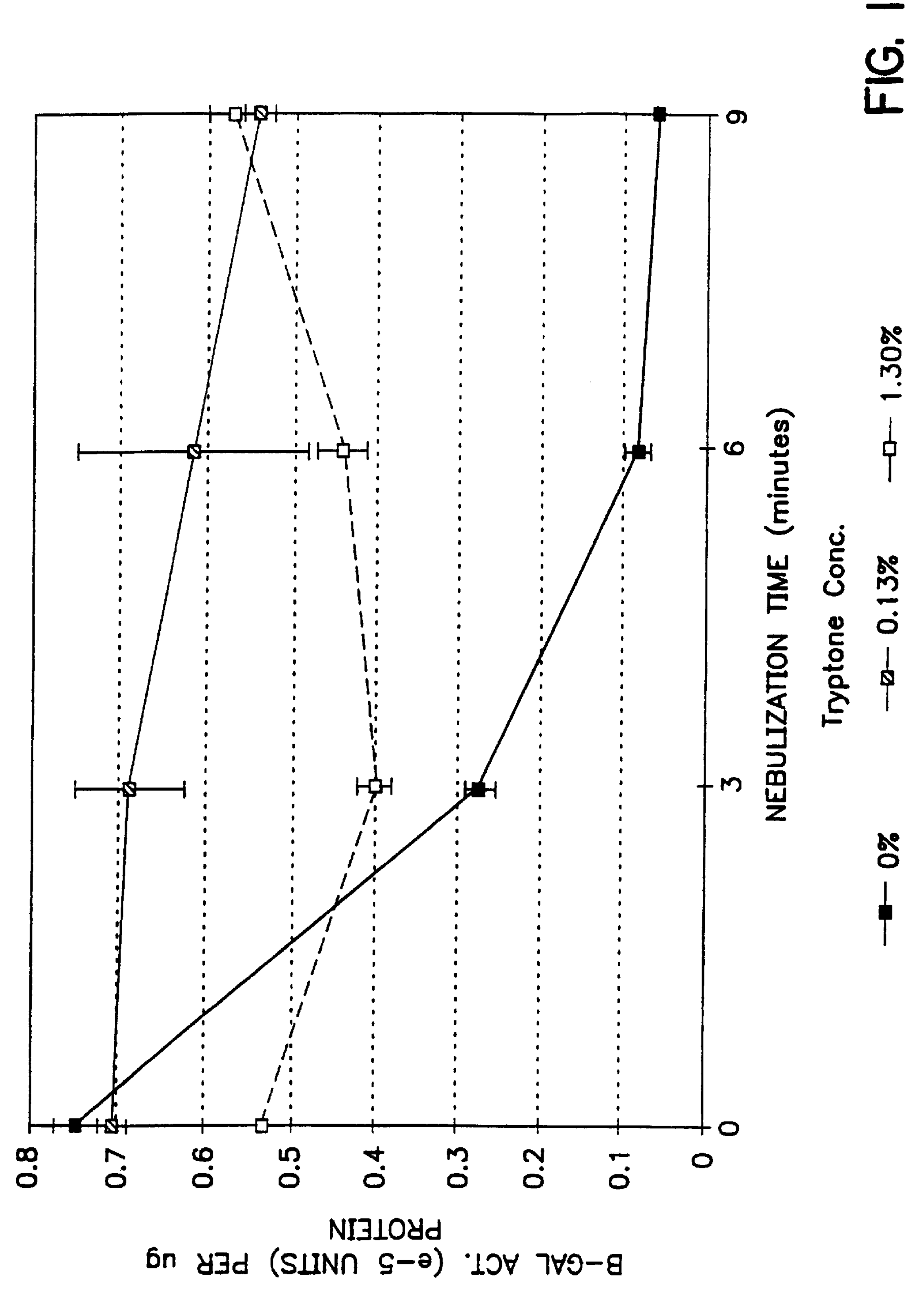
FIG. 1 shows that the addition of 1.3% tryptone to the nebulizer solution produced a similar, but intermediate, level of protection against nebulizer-induced losses.

The present invention is directed to a liposomal aerosol composition, comprising: (a) a pharmaceutical compound; (1) a cationic lipid, (3) a neutral co-lipid, and (4) tryptone. In one embodiment of this liposome aerosol composition, the pharmaceutical compound is a gene in the form of plasmid DNA. Representative examples of useful phospholipids include egg yolk phosphatidylcholine, hydrogenated soybean phosphatidylcholine, dimyristoyphosphatidylcholine, dilauroyl-phosphatylcholine, diolyeolyl-dipalmitoyleolylphosphatidylcholine, bis(guanidinium)tren-cholesterol and dipalmitoyl phosphatidylcholine. The co-lipid is generally a neutral phospholipid. Representative examples of suitable co-lipids include dioleoyphosphotidylethanolamine (DOPE), analogs of dioleoyphosphotidylethanolamine, and cholesterol. Typically, the tryptone is found in this composition in an amount sufficient to enhance transfection of a DNA:lipid suspension following nebulization. Generally, such concentrations of from about 0.1% to about 5%.

The present invention is also directed to a liposomal aerosol composition, comprising: (1) a pharmaceutical compound; (2) cationic lipid, (3) a neutral co-lipid, and (4) glutamic acid. In one embodiment of this liposome aerosol composition, the pharmaceutical compound is a gene. Representative examples of useful phospholipids include egg yolk phosphatidylcholine, hydrogenated soybean phosphatidylcholine, dimyristoyphosphatidylcholine, dilauroyl-phosphatylcholine, diolyeolyl-dipalmitoyleolylphosphatidylcholine, bis(guanidinium)-tren-cholesterol and dipalmitoyl phosphatidylcholine. Typically, the glutamic acid is found in this composition in an amount sufficient to enhance transfection of a DNA:lipid suspension following nebulization. Generally, such concentrations of from about 0.1% to about 5%.

The present invention is also directed to a nebulized cationic lipid:DNA suspension useful for lipid-DNA transfections, wherein said cationic lipid is bis (guanidinium)-tren-cholesterol and the neutral co-lipid is DOPE. Preferably, the bis(guanidinium)-tren-cholesterol/DOPE is contained in said suspension in a concentration relative to the plasmid DNA concentration determined to be optimal for transfection. The concentraton of the stable formulation depends on the relative concentrations of the three components, i.e., the plasmid DNA, the cationic lipid bis(guanidinium)-tren-cholesterol, and the neutral co-lipid DOPE. A preferred range of the plasmid DNA is from about 40 μg/ml to about 400 μg/ml. The optimal ratio of plasmid DNA to combined lipid (lipid formulation includes a 1:1 ratio of cationic lipid to neutral co-lipid) is approximately 1:3. However, slightly dfferent ratios often prove optimal for different applications or different plasmids, e.g., larger plasmids have a greater net charge and therefore require more lipid to neutralize this charge. Therefore, for 400 μg/ml DNA, one would use approximately 600 μg/ml of bis (guanidinium)-tren-cholesterol and 600 μg/ml of DOPE. Concentrations of bis(guanidinium)-tren-cholesterol up to about 1.5 mg/ml (when present in a 1:1 ratio of DOPE) should be stable in a formulation with plasmid DNA. In one embodiment of the nebulized cationic lipid:DNA suspension of the present invention, the ratio of DNA concentration to combined cationic lipid and neutral co-lipid concentration is about 1:1 to about 1:4.

The following examples are given for the purpose of illustrating various embodiments of the invention and are not meant to limit the present invention in any fashion.

EXAMPLE 1

Plasmid

The cytomegalovirus promoter (CMV) with the *E. coli* (β-galactosidase reporter gene (pCMVβ-gal) was used to assess mammalian cell expression. pCMVβ-gal (Clontech Laboratories, Inc., Palo Alto, Calif.) was obtained as a bacterial paste from Genzyme, Inc. and was purified on Qiagen columns (Qiagen, Inc., Chatsworth, Calif.).

EXAMPLE 2

Cationic Lipids

DL-EPC/DOPE, a 1:1 mixture of 1,2-dilauroyl-sn-glycero-3-ethylphosphocholine (DL-EPC) and dioleoyl phosphatidylethanolamine (DOPE; Avanti Polar Lipids, Alabaster, AL) was prepared prepared by mixing the DL-EPC (5 mg/ml chloroform) and with DOPE (5 mg/ml in chloroform) and dried under nitrogen. The lipid was then dissolved in t-butanol at 37° C., frozen at −80° C., and lyophilized for at least 24 hours. DC-CHOL/DOPE, a 1:1 mixture of 3β-[N-[(N',N'-dimethylamino) ethane] carbamoyl]cholesterol (DC-CHOL) and DOPE was prepared by dissolving the DC-CHOL in chloroform and then combining with DOPE. The lipid was then prepared in the same manner as the DL-EPC/DOPE. The lipids were stored at −20° C. until use. The lipid was then warmed to room temperature and swelled with Water For Irrigation (WFI) for at least 30 minutes prior to complexing with DNA.

EXAMPLE 3

Optimizing DNA to Lipid Ratios

Optimization of DNA to lipid ratio was determined by gel electrophoresis. When the negative DNA charge was completely neutralized by the cationic lipid, tissue culture transfection was maximized. By varying the ratio of DNA to lipid from 1:1 to 1:10 and running the complex on a 1% Agarose-TAE gel, the optimal ratio can be observed because the neutral Lipid:DNA complex does not migrate.

EXAMPLE 4

Tissue Culture

A549 cells (human lung carcinoma with epithelial-like morphology) were cultured in Dulbecco's Modified Essential Medium (D-MEM) supplemented with 10% defined fetal bovine serum (FBS), 2 mM L-glutamine, and 50 μg/ml gentamicin.

EXAMPLE 5

Transfection

A549 cells were plated at $1.5\times10^5$ cells/35-mm dish the day prior to transfection. Cells were ~80% confluent at the time of transfection. An equal volume of 2× Opti-mem I Reduced Serum Media (Opti-mem; Gibco-BRL, Grand Island, N.Y.) was added to each 175 μl aliquot from the nebulizer reservoir and then brought up to a final volume of 3.5 ml with Opti-mem (1×). Opti-mem is a modification of Eagle's Minimum Essential Medium with growth factors added and is ideal for cationic-lipid-DNA transfections. Immediately prior to transfection, cells were rinsed twice with Opti-mem and then overlayed with the 1 ml of the transfection solution per well (3 wells were transfected for each time point). After 24 hours the solution was removed, the cells were rinsed 2 times with Opti-mem, and 1 ml A549 medium was added. The cells were then incubated for an additional 24 hours, rinsed two times with PBS and then lysed.

EXAMPLE 6

Quantitative Analysis of β-galactosidase Transfection Efficiency

A549 cells were lysed with 500 μl of 0.1M Tris-HCl containing 0.5% Triton X-100. Cell debris was removed by centrifugation and the protein concentration of the lysate was determined by a protein assay using bicinchronic acid (BCA Protein Assay; Pierce, Rockford, Ill.). The β-galactosidase activity was quantified by using a chlorophenolred-β-D-galactopyranoside (CPRG; Boehringer Mannheim, Indianapolis, Ind.) solution containing magnesium chloride and β-mercaptoethanol in phosphate buffered saline (PBS). A 100 μl aliquot of lysate was added to a well of a 96-well plate and an equal volume of CPRG solution was added. The samples and standards were incubated at 37° C. and then read on the Dynatech MR5000 microtiter plate reader (Dynatech Laboratories, Inc., Chantilly, Va.).

EXAMPLE 7

Results

Certain constituents, when added to the lipid:DNA suspension prior to nebulization, stabilized the transfection potential of these formulations significantly. This results in a many-fold increase in the quantity of biologically active gene therapeutic agent being delivered.

Over several experiments, the addition of 0.13% tryptone, an enzymatic (tryptic) digest of casein, to the nebulizer solution resulted in 105%, 100% and 93% retention of the transfection activity of the control (unnebulized) material in an in vitro assay using A549 human lung tumor cells when aliquots of the nebulizer-cycled material were removed from the nebulizer reservoir at 3, 6 and 9 minutes of nebulization respectively at a flow rate of 15 L/min and a starting volume of 5 ml. This compares to a 51%, 13% and 6% retention of transfection activity for the control (no tryptone added). An addition of 1.3% tryptone produced a similar, but intermediate, level of protection against nebulizer-induced losses (see FIG. 1).

These results were obtained for a formulation consisting of DL-EPC/DOPE complexed with pCMVβ-GAL plasmid DNA (for the expression of β-galactosidase). Similar stabilization of transfection activity was achieved when this experiment was repeated twice more. The nebulizer used was a modified Puritan Bennett 1600 nebulizer (Carlsbad, Calif.)—one tube from the twin jets was removed—this nebulizer is referred to as the Puritan Bennett 1600 single jet (PB sj). The control nebulizer solution consisted of 200 μg of pCMVβ-GAL and 700 μg of DL-EPC/DOPE complexed in Water for Irrigation (WFI; Baxter) in a total volume of 5 mls. The nebulizer solution with 0.13% tryptone contained the same amount of plasmid DNA and lipid. A 50 μl aliquot of a 13% tryptone stock solution (13% w/v in WFI) was added to the nebulizer solution after the DNA and lipid had complexed for 15 minutes (the final volume remained at 5 mls). The nebulizer solution with 1.3% tryptone also contained the same amount of plasmid DNA and lipid. A 0.5 ml aliquot of a 13% tryptone stock solution (13% w/v in WFI) was added to the nebulizer solution after the DNA and lipid had complexed for 15 minutes (the final volume after the addition of the tryptone was 5 mls).

Figure 2:
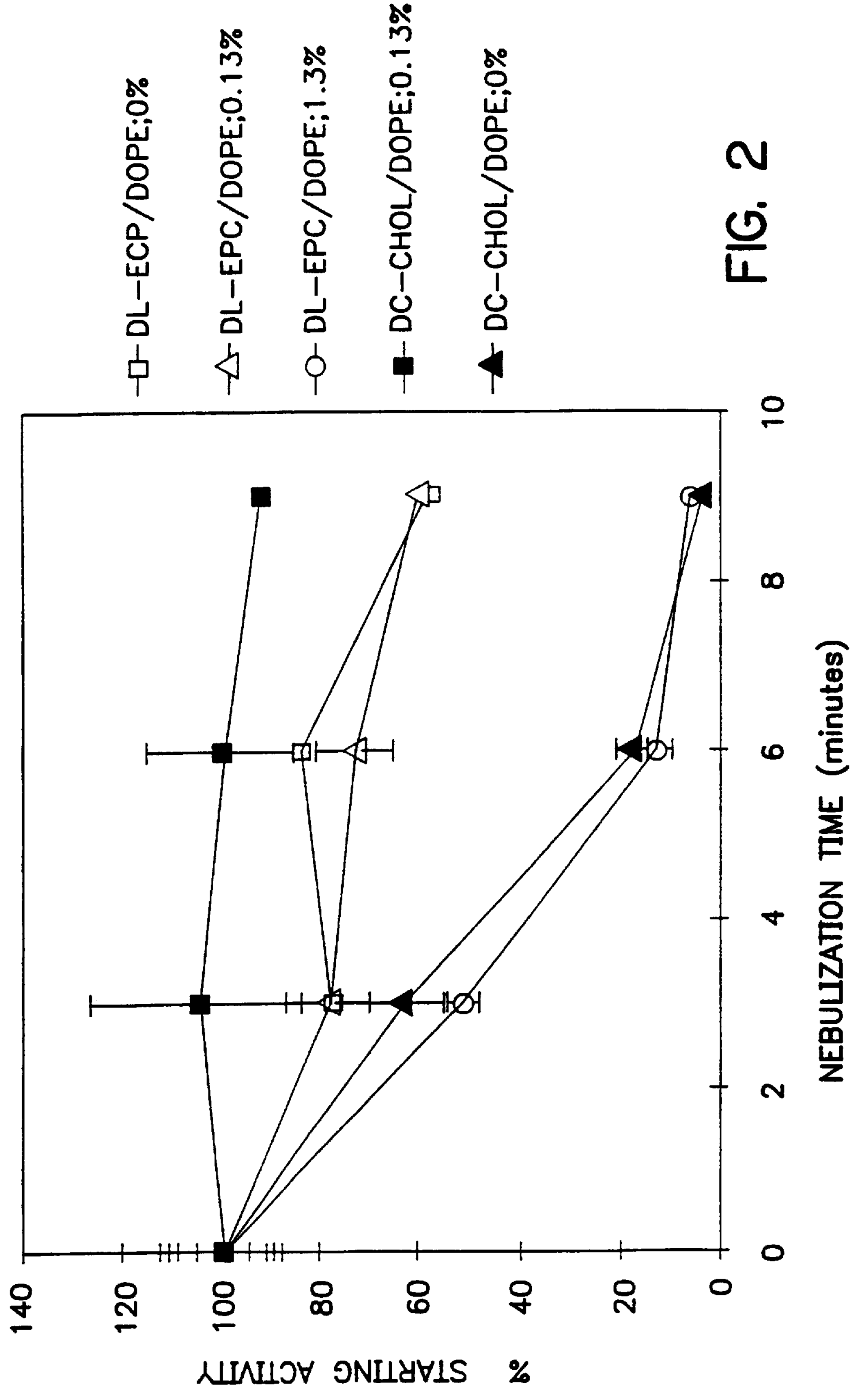
FIG. 2 shows a comparison of the effects of tryptone on the nebulizer-induced losses encountered with different lipids.

In addition, a similar stabilization was achieved when using a formulation consisting of DC-CHOL/DOPE and pCMVβ-GAL, indicating that the effect is apparently not dependent upon a specific cationic lipid for lipid formulation. The control nebulizer solution consisted of 200 μg of pCMVβ-GAL and 800 μg of DC-CHOL/DOPE complexed in WFI in a total volume of 5 mls. The nebulizer solution with 0.13% tryptone contained the same amount of plasmid DNA and lipid. A 50 μl aliquot of a 13% tryptone stock solution (13% w/v in WFI) was added to the nebulizer solution after the DNA and lipid had complexed for 15 minutes (the final volume remained at 5 mls). The nebulizer solution with 1.3% tryptone also contained the same amount of plasmid DNA and lipid. A 0.5 ml aliquot of a 13% tryptone stock solution (13% w/v in WFI) was added to the nebulizer solution after the DNA and lipid had complexed for 15 minutes (the final volume after the addition of the tryptone was 5 mls). A comparison of the effects of tryptone on the nebulizer-induced losses encountered with both lipids is illustrated in FIG. 2.

Figure 3:
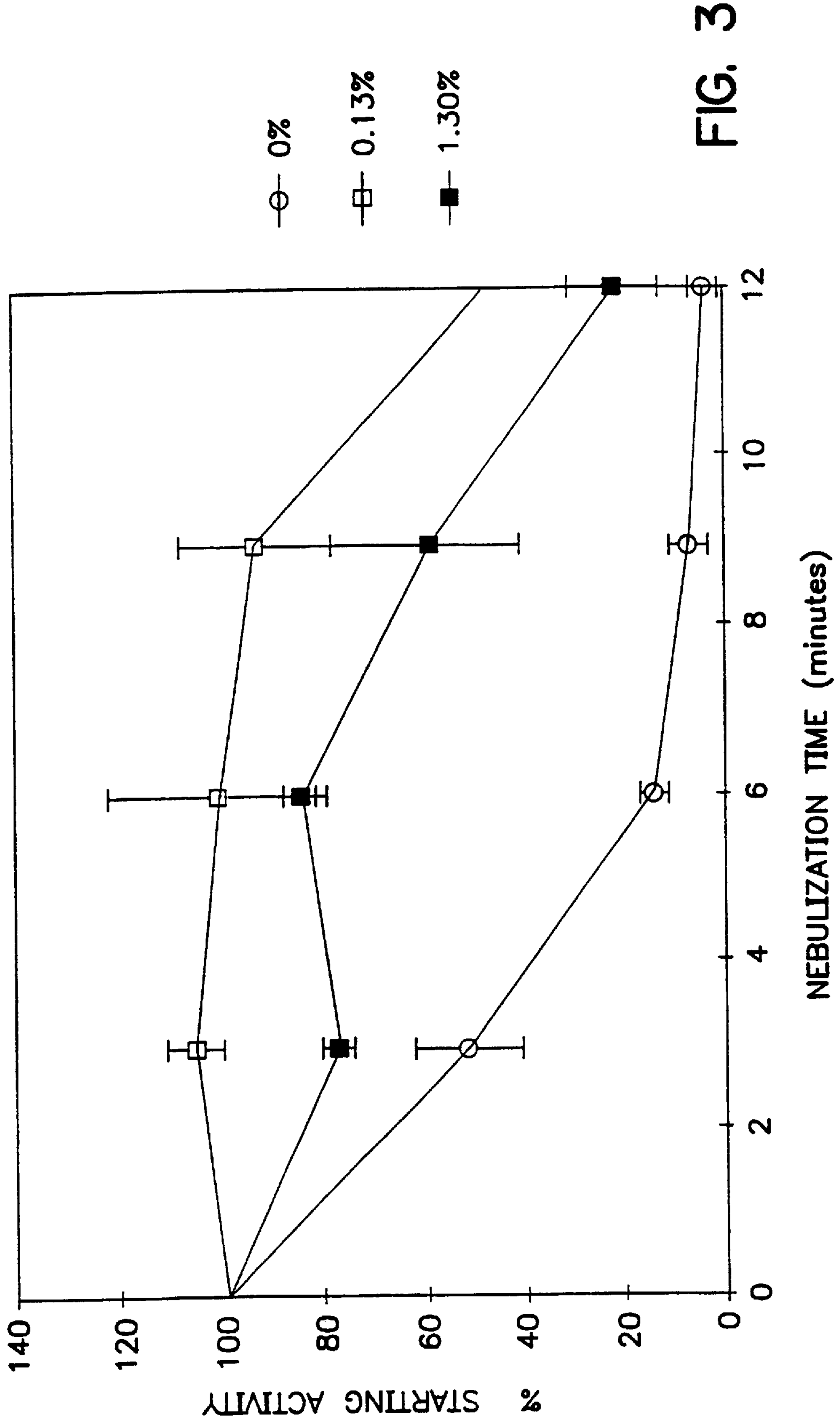
FIG. 3 shows that glutamic acid also provided a significant degree of protection against nebulizer-induced loss of cell transfection activity when present at concentrations equivalent to the concentrations in tryptone.

Since tryptone is composed of a number of components, whether one or more specific components was responsible for the observed aerosol stability was examined. Glutamic acid, a major amino acid component of tryptone, also provided a significant degree of protection against nebulizer-induced loss of cell transfection activity when present at concentrations equivalent to the concentrations that would have been present in the concentration of tryptone found effective in the above experiments (see FIG. 3). This experiment was conducted in the same fashion as the previously described experiments using DC-cholesterol:DOPE:pCMVβ-GAL and glutamic acid in the concentrations of 0.221 mg/ml and 0.975 mg/ml and has also been replicated. The control nebulizer solution consisted of 200 μg of pCMVβ-GAL and 800 μg of DC-Chol/DOPE complexed WFI in a total volume of 5 mls. The nebulizer solution containing 0.221 mg/ml glutamic acid also contained the same amount of plasmid DNA and lipid. A 0.227 ml aliquot of a 4.875 mg/ml glutamic acid stock solution (in WFI) was added to the nebulizer solution after the DNA and lipid had complexed for 15 minutes (the final volume after the addition of the glutamic acid was 5 mls). The nebulizer solution containing 0.975 mg/ml glutamic acid also contained the same amount of plasmid DNA and lipid. A 1 ml aliquot of a 4.875 mg/ml glutamic acid stock solution (in WFI) was added to the nebulizer solution after the DNA and lipid had complexed for 15 minutes (the final volume after the addition of the glutamic acid was 5 mls).

EXAMPLE 8

Plasmid

The cytomegalovirus promoter (CMV) with the *E. coli* (β-galactosidase reporter gene (pCMVβ-gal) was used to assess mammalian cell expression. pCMVβ-gal (Clontech Laboratories, Inc., Palo Alto, Calif.) was obtained as a bacterial paste from Genzyme, Inc. and was purified on Qiagen columns (Qiagen, Inc., Chatsworth, Calif.).

EXAMPLE 9

Cationic Lipids

BGTC/DOPE, a 1:1 mixture of bis(guanidinium)-tren-cholesterol and dioleoyl phosphatidyl-ethanolamine (DOPE; Avanti Polar Lipids, Alabaster, Al.) was prepared by mixing the DL-EPC (5 mg/ml chloroform) and with DOPE (5 mg/ml in chloroform) and dried under nitrogen. The lipid was then dissolved in t-butanol at 37° C., frozen at −80° C., and lyophilized for at least 24 hours. DC-CHOL/DOPE, a 1:1 mixture of of 3β-[N-[(N',N'-dimethylamino)ethane]

carbamoyl]cholesterol (DC-CHOL) and DOPE was prepared by dissolving the DC-CHOL in chloroform and then combining with DOPE. The lipid was then prepared in the same manner as the BGTC/DOPE. The lipids were stored at −20° C. until use. The lipid was then warmed to room temperature and swelled with WFI for at least 30 minutes prior to complexing with DNA.

EXAMPLE 10

Optimizing DNA to Lipid Ratios

Optimization of DNA to lipid ratio was determined by gel electrophoresis. When the negative DNA charge is completely neutralized by the cationic lipid, tissue culture transfection is maximized. By varying the ratio of DNA to lipid from 1:1 to 1:10 and running the complex on a 1% Agarose-TAE gel, the optimal ratio can be observed because the neutral lipid:DNA complex does not migrate.

EXAMPLE 11

Tissue Culture

A549 cells (human lung carcinoma with epithelial-like morphology) were cultured in Dulbecco's Modified Essential Medium (D-MEM) supplemented with 10% defined fetal bovine serum (FBS), 2 mM L-glutamine, and 50 μg/ml gentamicin.

EXAMPLE 12

Transfection

A549 cells were plated at $1.5\times10^5$ cells/35-mm dish the day prior to transfection. Cells were ~80% confluent at the time of transfection. An equal volume of 2× Opti-mem I Reduced Serum Media (Opti-mem; Gibco-BRL, Grand Island, N.Y.) was added to each 175 μl aliquot from the nebulizer reservoir and then brought up to a final volume of 3.5 ml with Opti-mem (1×). Opti-mem is a modification of Eagle's Minimum Essential Medium with growth factors added and can be used for cationic-lipid-DNA transfections. Immediately prior to transfection, cells were rinsed twice with Opti-mem and then overlayed with the 1 ml of the transfection solution per well (3 wells were transfected for each time point). After 24 hours the solution was removed, the cells were rinsed 2 times with Opti-mem, and 1 ml A549 medium was added. The cells were then incubated for an additional 24 hours, rinsed two times with PBS and then lysed.

EXAMPLE 13

Quantitative Analysis of β-galactosidase Transfection Efficiency

A549 cells were lysed with 500 μl of 0.1M Tris-HCl containing 0.5% Triton X100. Cell debris was removed by centrifugation and the protein concentration of the lysate was determined by a protein assay using bicinchronic acid (BCA Protein Assay; Pierce, Rockford, Ill.). The β-galactosidase activity was quantified by using a chlorophenolred-β-D-galactopyranoside (CPRG; Boehringer Mannheim, Indianapolis, Ind.) solution containing magnesium chloride and β-mercaptoethanol in phosphate buffered saline (PBS). A 100 μl aliquot of lysate was added to a well of a 96-well plate and an equal volume of CPRG solution was added. The samples and standards were incubated at 37° C. and then read on the Dynatech MR5000 microtiter plate reader (Dynatech Laboratories, Inc., Chantilly, Va.).

EXAMPLE 14

Bis(guanidinium)-tren-cholesterol Stabilization of Transfection

Figure 4:
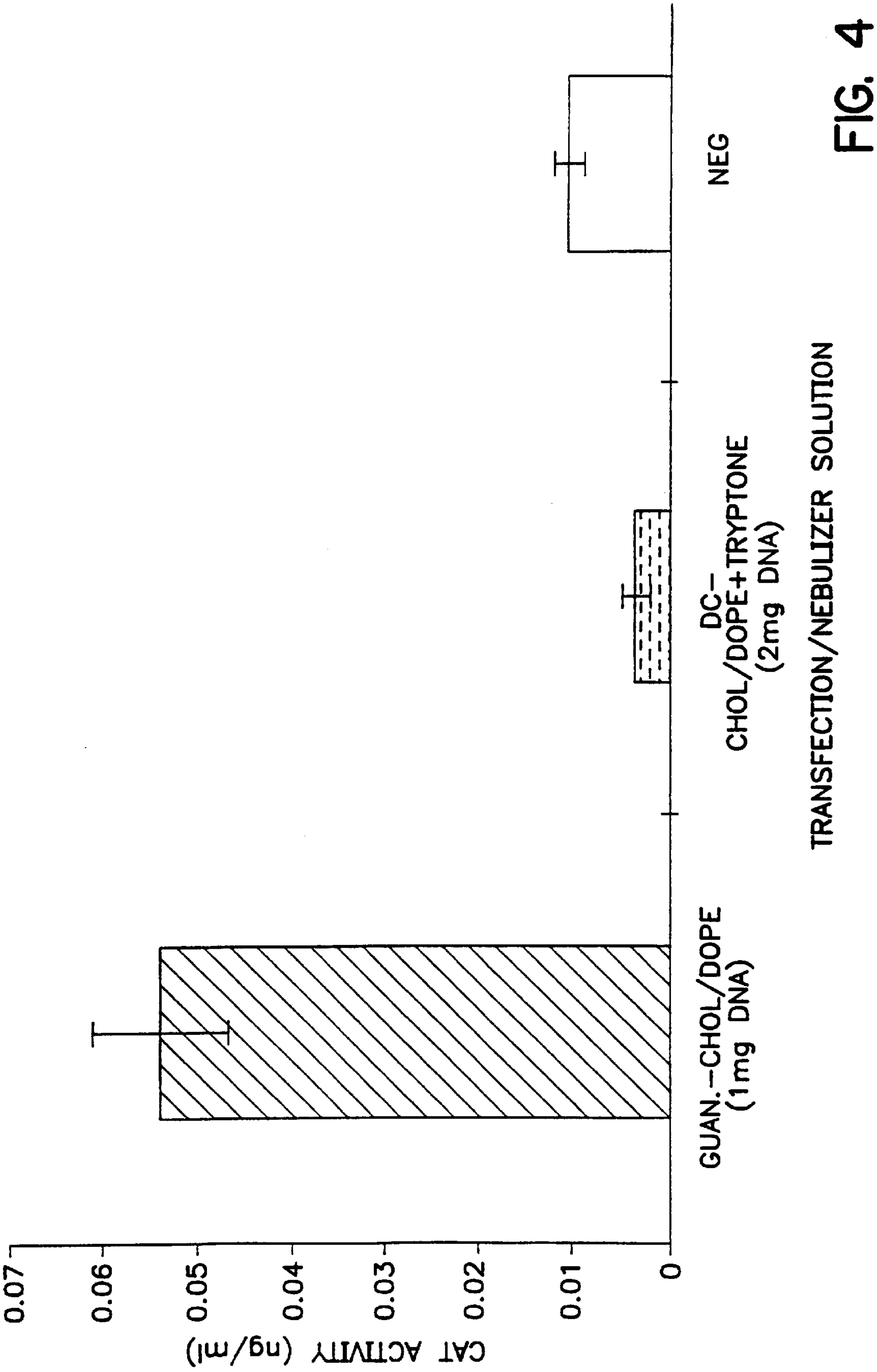
FIG. 4 shows the in vivo aerosol treatment of Balb/C mice. In this experiment, animals were subjected to either intermittent aerosol exposure of the lipid:DNA (chloramphenicol acetyl transferase gene) formulations indicated or to no aerosol exposure (NEG). The exposure was accomplished by placing the animals in an enclosed chamber attached to a Puritan Bennett 1600 single jet nebulizer and providing 1 minute of aerosol followed by a 9 minute delay to allow the animals to breath the aerosol before beginning the cycle again. The nebulizer was driven by compressed air containing 5% carbon dioxide to enhance deep breathing. This was repeated until all of the nebulizer fluid was depleted (approx. 16 hours). Animals were sacrificed 48 hours after the end of the aerosol treatment, lungs were removed and tissues were extracted and assayed (by ELISA) for the expression of CAT activity.

The present invention shows that certain constituents, when added to the lipid:DNA suspension prior to nebulization, significantly stabilize the transfection potential of these formulations. More specifically, formulations containing one particular cationic lipid appear to be significantly more stable during the process of nebulization than previously tested lipids. This lipid, bis(guanidinium)-tren-cholesterol (BGTC) has been reported (Oudrhiri et al., 1997) as a potential candidate for gene therapy. Oudrhiri et al., however, only used an intratracheal instillation approach for administering the lipid:DNA formulations and did not examine aerosol delivery. These fromulations are effective in vivo (in mouse lungs) as a gene therapy agent when nebulized. These results are illustrated in FIG. 4.

In two experiments, the use of bis(guanidinium)-trencholesterol resulted in an average of 98%, 95% and 84% retention of the transfection activity of the control (unnebulized) material in an in vitro assay using A549 human lung tumor cells when aliquots of the nebulizer-cycled material were removed from the nebulizer reservoir at 3, 6 and 10 minutes of nebulization respectively at a flow rate of 15 L/min and a starting volume of 5 ml. This compares to a 40%, 15.7% and 13.5% retention of transfection activity for another commonly used cationic lipid (DC-CHOL/DOPE).

Figure 5:
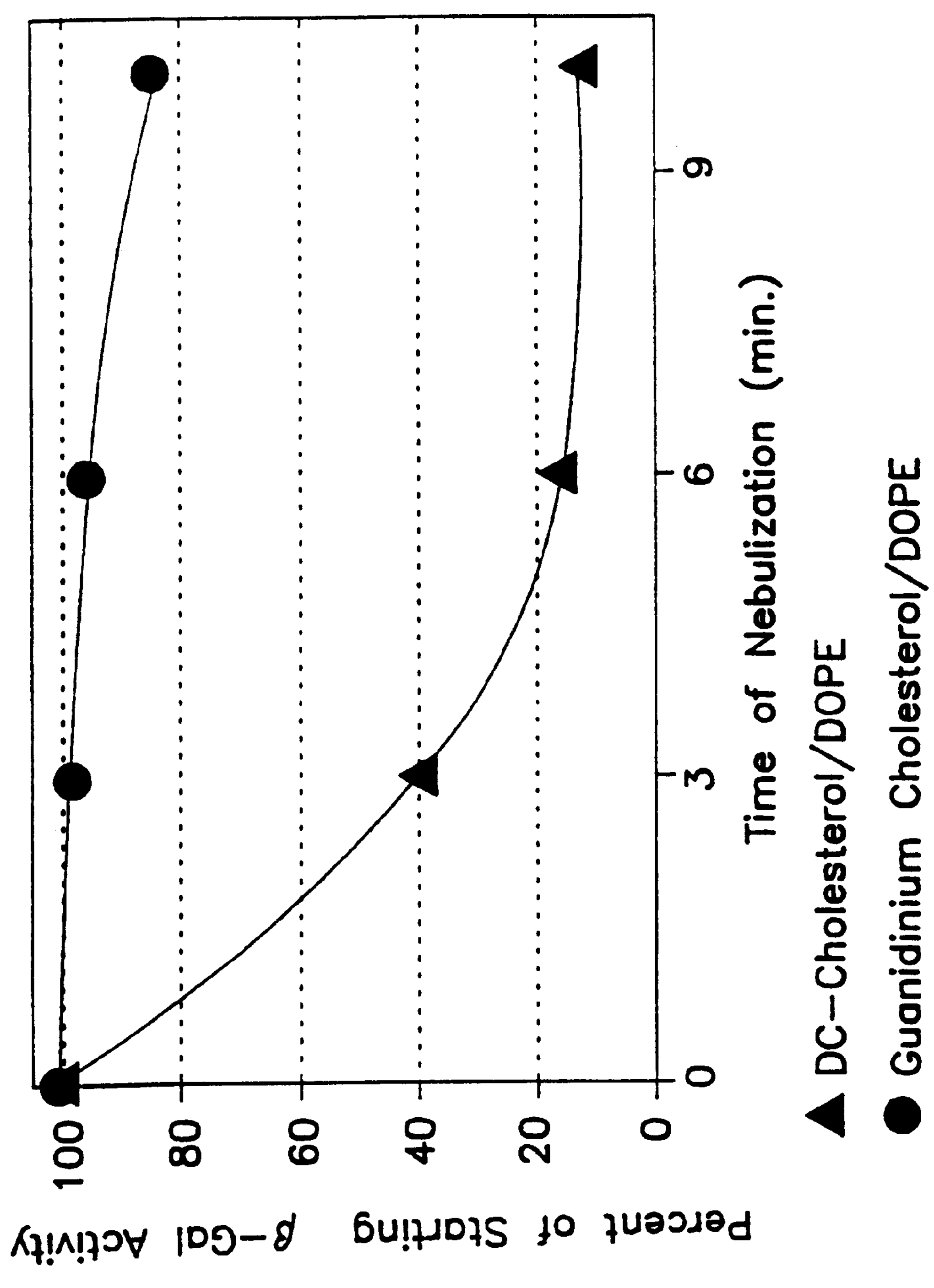
FIG. 5 shows the effect of cationic lipid on transfection stability during nebulization. As detailed below, the lipid:DNA formulations were subjected to the process of nebulization for the durations shown prior to samples being taken from the nebulizer reservoir and qualitatively monitored in an in vitro transfection assay using A549 (human lung cancer) cells in culture. The activity of the guanidinium cholesterol/DOPE represents the mean results from two experiments and is significantly more stable during nebulization than DC-cholesterol/DOPE (shown) and a number of other commonly used lipids that are not shown in this graph.

The degree of loss observed with DC-CHOL/DOPE is very typical of that observed for a number of cationic lipids commonly used for gene therapy applications and currently in use in clinical trials. This data is summarized in FIG. 5. The nebulizer used was a modified Puritan Bennett 1600 nebulizer (Carlsbad, Calif.)—one tube was removed from one of the twin jets. This nebulizer is called the Puritan Bennett 1600 single jet (PB sj). The control nebulizer solution consisted of 200 μg of pCMVβ-GAL and 700 μg of the cationic lipid/co-lipid formulation complexed in Water for Irrigation (WFI; Baxter) in a total volume of 5 mls.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A liposomal aerosol composition, comprising:

(a) a plasmid DNA containing a gene;

(b) a cationic lipid;

(c) a neutral co-lipid; and (d) tryptone.

2. The liposome aerosol composition of claim 1, wherein said cationic and neutral co-lipids are selected from the group consisting of egg yolk phosphatidylcholine, hydrogenated soybean phosphatidylcholine, dimyristoylphosphatidylcholine, dilauroylphosphatidylcholine, dioleoylphosphatidylcholine, dioleoylphosphatidylethanolamine, bis(guanidinium)-tren-cholesterol, and dipalmitoylphosphatidylcholine.

3. The liposome aerosol composition of claim 1, wherein said tryptone is found in said composition in a concentration of from about 0.01% to about 5%.

* * * * *

UNITED STATES PATENT AND TRADEMARK OFFICE

CERTIFICATE OF CORRECTION

PATENT NO. : 6,106,859

DATED : August 22, 2000

INVENTOR(S) : Densmore, Jr., et al.

It is certified that error appears in the above-identified patent and that said Letters Patent is hereby corrected as shown below:

In Column 2, line 22, "each minutes" should read --each 10 minutes--.

In Column 3, line 24, "soybean phosphohatidylcholine" should read --soybean phosphoatidylcholine--.

In Column 3, line 26, "phosphophatylcholine, diolyeolyl" should read --phosphophatylcholine, diolyeolyl--.

In Column 3, line 27, "dipalmitoyleolylphosphatidylcholine" should read --phosphatidylcholine--.

In Column 3, line 27, "bis(guanidinium) tren" should read --bis(guanidinium)-tren--.

In Column 3, line 46, "dipalmitoyleolyl-" should be removed.

In Column 4, line 31, "prepared" should be removed."

UNITED STATES PATENT AND TRADEMARK OFFICE

CERTIFICATE OF CORRECTION

PATENT NO. : 6,106,859

DATED : August 22, 2000

INVENTOR(S) : Densmore, Jr., et al.

It is certified that error appears in the above-identified patent and that said Letters Patent is hereby corrected as shown below:

In Column 6, line 62, "Al." should read --AL--.

In Column 7, line 48, "X100" should read --X-100--.

Signed and Sealed this

Twenty-ninth Day of May, 2001

Attest:

NICHOLAS P. GODICI

Attesting Officer

*Acting Director of the United States Patent and Trademark Office*